United States Patent [19]

Suzuki et al.

[11] Patent Number: 5,615,518
[45] Date of Patent: Apr. 1, 1997

[54] SPROUTED VEGETABLE SEEDS STERILIZING METHOD, AND SPROUTED VEGETABLES CULTIVATING METHOD

[75] Inventors: Tomosaburo Suzuki, Kanagawa-ken; Tsuneo Takizawa, Hachioji, both of Japan

[73] Assignee: Daisey Kikai Kabushiki Kaisha, Tokyo, Japan

[21] Appl. No.: 561,115

[22] Filed: Nov. 20, 1995

Related U.S. Application Data

[63] Continuation of Ser. No. 202,452, Feb. 28, 1994, abandoned.

[30] Foreign Application Priority Data

Mar. 13, 1993 [JP] Japan ..................... 5-091790

[51] Int. Cl.$^6$ ................. A01G 1/00; A01G 7/00
[52] U.S. Cl. ........................... 47/58; 47/DIG. 9
[58] Field of Search ................. 47/58, 57, DIG. 9

[56] References Cited

FOREIGN PATENT DOCUMENTS 217407A   1/1985   Germany .
1230482A  1/1983   U.S.S.R. .

*Primary Examiner*—Douglas W. Robinson
*Assistant Examiner*—Elizabeth F. McElwain
*Attorney, Agent, or Firm*—Oblon, Spivak, McClelland, Maier & Neustadt, P.C.

[57] ABSTRACT

An effective method for sterilizing seeds for sprouted vegetables and a sprouted vegetables cultivating method in which the growth of sprouted vegetables is promoted, while restraining the occurrence of their putrefaction caused by the breeding of microorganisms, are provided.

18 Claims, No Drawings

SPROUTED VEGETABLE SEEDS STERILIZING METHOD, AND SPROUTED VEGETABLES CULTIVATING METHOD

This application is a Continuation of application Ser. No. 08/202,452, filed on Feb. 28, 1994, now abandoned.

BACKGROUND OF THE INVENTION (1) Technical Field

The present invention relates to a method for sterilizing seeds for sprouted vegetables, for example seeds for various kinds of sprouts such as black mung bean sprouts, mung bean sprouts, soybean sprouts or alfalfa sprouts, and KAI-WARE radish or the likes, and a method for cultivating sprouted vegetables.

(2) Background Technology

As a problem of the so-called sprouted vegetables, i.e. various kinds of sprouts, which will be good to eat after their seeds are sprouted and somewhat grown up, it is important how to promote their rearing. Although sprouted vegetables will be cultivated at a temperature and humidity suitable for their sprouting and growth, such a rearing environment is also an environment suitable for the breeding of various kinds of microorganisms.

Seeds are generally contaminated on the outer surface of their shells and sometimes on the inner surface thereof by microorganisms, and this contamination becomes a factor for putrefying sprouted vegetables in their cultivation. In particular, in a case of sprouts, seeds must be sprouted and grown up in a high temperature and high humidity environment while supplying water thereto at all times, and under such a situation, it is therefore very difficult to restrain the breeding of microorganisms.

In a case where sprouted vegetables are cultivated in the prior art, seeds are washed with water so as to remove microorganisms therefrom or subjected to a sterilizing treatment using chlorine or other chemicals, before their soaking which comprises dipping seeds in warm water for the purpose of promoting their sprouting. However, it is difficult to destroy microorganisms effectively, without damaging the life activity performing abilities of seeds as a living thing, i.e. their sprouting and growing abilities, and in addition, it is not permitted to use strong chemicals because sprouted vegetables are foods which are often eaten fresh.

In the prior art, accordingly, microorganisms are inevitably permitted to breed in some extent when sprouted vegetables are reared, and as a result, it is unavoidable that the putrefaction of sprouted vegetables is caused by microorganisms in the course of their rearing and the preservation of sprouted vegetables after their harvest is worsened. Namely, there is no reliable way, excepting the way of getting seeds free from being contaminated with microorganisms which will cause their putrefaction or the way of subjecting seeds to some sterilizing treatment with chemicals, and such is the present state of things.

OBJECT OF THE INVENTION

The present invention is intended to provide an effective method for sterilizing seeds for sprouted vegetables, for the purpose of supplying seeds which can be grown to sprouted vegetables, with no trouble caused by the breeding of microorganisms. In particular, it is an object of the present invention to provide a method for sterilizing seeds for sprouted vegetables, which can effectively destroy microorganisms, without using any chemicals, and which can further supply seeds capable of being preserved for a long period of time after their sterilizing treatment.

Furthermore, it is an object of the present invention to provide a novel method for cultivating sprouted vegetables, which can promote the rearing of sprouted vegetables, with restraining the occurrence of their putrefaction due to the breeding of microorganisms.

SUMMARY OF THE INVENTION

For the purpose of solving the aforementioned problems in the sterilizing treatment of seeds for sprouted vegetables, according to the present invention, there is adopted a sprouted vegetable seeds sterilizing method comprising bringing seeds into contact with a high temperature of 70° C. or more that is effective for pasteurizing microorganisms existing on the surface of seeds, and sometime in the inside thereof after invaded from the external wounds or broken portions of seeds, without damaging the life functions of seeds' embryos, with accuracy and only for a proper period of time, and then quenching the seeds quickly.

As for the said temperature of 70° C. or more to which seeds for sprouted vegetables are to be exposed and time of exposure to that temperature in the present invention, optimum values will be concretely selected depending upon an object of sprouted vegetable seeds. In order to expose seeds for sprouted vegetables to such a high temperature, they may be dipped in hot water having a predetermined temperature of 70° C. or more, or exposed to steam. When it is not required to give humidity to seeds, dry heat such as heated air or combustion gas may be used.

As occasion demands, sprouted vegetable seeds may be exposed to a temperature of several hundreds °C. in a moment, for example, to a flame having a temperature of 400°~600° C. for 0.5~1 second. In addition, as to the said temperature and time of exposure, values to be selected will vary depending on whether a high temperature of 70° C. or more is given by dry heat such as heated air or by wet heat such as hot water or steam.

After the heating treatment, the sprouted vegetable seeds are quickly quenched, in order that any obstacle due to heat is not left in the seeds as a living thing exposed to an optimum temperature of 70° C. or more for a predetermined period of time and with accuracy. For the same purpose, it is also effective to subject seeds to a preheating treatment before they are exposed to a predetermined high temperature.

In the sprouted vegetable seeds sterilizing method according to the present invention, seeds for sprouted vegetables are exposed to a high temperature of 70° C. or more for a short period of time and then quenched quickly, as mentioned above, whereby they can be effectively sterilized, without damaging the function of seeds as a living thing. And, in a case where the heat to which seeds are to be exposed is dry heat such as heated air, seeds are quenched quickly by cold air or the like after the heating treatment, and the seeds get into a condition suitable for preservation as sterilized.

These seeds under preservation will be directly taken out and they can be used as sprouted vegetable seeds which can be cultivated, without causing any putrefaction of them by the breeding of microorganisms.

In order to achieve the aforementioned purpose on the cultivation of sprouted vegetables, furthermore, according to the present invention, there is adopted a method comprising cultivating seeds for sprouted vegetables, after they are subjected to a sterilizing treatment comprising exposing seeds before their rearing to a high temperature of 70° C. or more for a short period of time and then quenching the seeds quickly.

A manner of exposing seeds to a high temperature of 70° C. or more is the same as mentioned above.

In the sprouted vegetables cultivating method according to the present invention, sprouted vegetable seeds are exposed to a high temperature of 70° C. or more for a short period of time, as mentioned above, whereby microorganisms which become an obstacle for rearing sprouted vegetables can be remarkably destroyed and therefore, the putrefaction of sprouts due to the breeding of microorganisms during their rearing can be extremely reduced.

Since sprouted vegetables reared by the cultivating method according to the present invention get into a condition that microorganisms breed less, moreover, it is possible, according to the present invention, to harvest sprouted vegetables capable of being preserved for a long period of time.

Since seeds subjected to a sterilizing treatment at a high temperature of 70° C. or more are used for cultivation by the sprouted vegetables cultivating method according to the present invention, furthermore, a further sterilizing treatment using chlorine or the like applied to sprouted vegetables in the course of their cultivation, for example in the soaking or intermediate sterilizing treatment, acts effectively upon microorganisms which are weakened, but live still, whereby the putrefaction of sprouted vegetables can be remarkably reduced.

DETAILED DESCRIPTION OF THE PREFERRED EMBODIMENTS

The sprouted vegetable seeds sterilizing method and the sprouted vegetables cultivating method according to the present invention will be concretely described in accordance with their preferred embodiments.

In the sprouted vegetable seeds sterilizing method according to the present invention, at first, seeds for sprouted vegetables are exposed to a high temperature of 70° C. or more for a short period of time, for instance for a short period to several tens seconds in such a range that embryos existing in the seeds are not damaged, and then the seeds are quenched quickly.

As for the said temperature and time of exposure to that temperature, optimum values will be concretely selected depending upon an object of seeds. As a medium by which seeds are exposed to such high temperature, there can be used wet heat such as heated water or steam or dry heat such as heated air or heated gas.

In a case where seeds for sprouted vegetables are subjected to a sterilizing treatment by dry heat and quenched quickly by cold air or the like, the seeds can be preserved as sterilized and they can be immediately used for cultivation in needs because their humidity is not increased after such treatment and they are not deteriorated or putrefied during the preservation.

In the sterilizing treatment according to the present invention, in general, the higher the temperature to which sprouted vegetable seeds are to be exposed is, the shorter the time of exposure becomes. However, the manner for giving heat to sprouted vegetable seeds will depend upon whether wet heat or dry heat is used, and the temperature and time which have no bad influence upon the life of sprouted vegetable seeds as a living thing will also vary as mentioned above.

Combinations of the temperature and time which are applicable to the high-temperature sterilizing treatment of seeds for sprouted vegetables, according to the present invention, will be generally exemplified for a standard as follows.

| | |
|---|---|
| 90° C. | about 10 seconds |
| 80° C. | 10–20 seconds |
| 70° C. | 20–30 seconds |

Since the selected temperature and time must be accurate because the object is a living thing, seeds are accurately exposed to a predetermined temperature for a given period of time. It is therefore important to put the seeds into a water tank kept nearly at normal temperature after that heating so that they are quickly quenched nearly to normal temperature, and also to preheat then below to 45° C. as occasion demands.

Furthermore, it is important to expose seeds to a predetermined temperature uniformly as they are stirred during the heating sterilization. In short, it is the point to effectively destroy microorganisms on the outer surface of seed shells or on the injured or broken portions thereof, without damaging the life function of seed embryos.

In the next place, the sprouted vegetables cultivating method according to the present invention will be concretely described in accordance with its preferred embodiment.

In a case where seeds are sprouted and grown up, thereby making sprouted vegetables, the seeds are usually subjected to the so-called soaking which comprises dipping them in warm water having a temperature of about 30°–40° C.

The present invention comprises, before the afore-mentioned soaking step, carrying out a sterilizing treatment comprising exposing seeds to the aforesaid high temperature of 70° C. or more. Then, the seeds which have been subjected to the sterilizing treatment as mentioned above will be cultivated after they are passed through the same soaking step as in the prior art.

In the soaking or intermediate sterilizing treatment carried out in the course of their cultivation, a further sterilizing treatment using chlorine or the like is carried out.

The effect of said further sterilizing treatment applied in the course of their cultivation will be remarkably revealed in the sprouted vegetables cultivating method according to the present invention. That reason will be understood to be that the said further sterilizing treatment using clorine or the like acts effectively upon microorganisms which are weakened, but not destroyed by the high-temperature treatment.

In addition, when seeds are heated by hot water or steam, they are given humidity and therefore the soaking time will vary.

A manner for carrying out the sterilizing treatment comprising exposing seeds to a high temperature of 70° C. or more and then quenching the seeds quickly, which is applicable in the sprouted vegetables cultivating method according to the present invention, is the same as mentioned above. However, an optimum temperature and treatment time can not be absolutely determined because the kinds and quantitys of microorganisms deposited on seeds vary depending on the growing districts of seeds and the occasional growing grades thereof, even in a case of the same kind of seeds. So, the temperature will be concretely selected on each occasion.

It is important to adopt a new method comprising cultivating seeds for sprouted vegetables which have been exposed to a high temperature of 70° C. or more and then quenched quickly.

The test results in a case where the method according to the present invention which comprises exposing seeds to a high temperature of 70° C. or more for a short period of time and rearing the seeds has been applied to the cultivation of mung bean sprouts, is given by way of example in Table 1.

In Table 1, Sample Nos. 3 and 4 represent, for comparison, the data obtained on the seeds which have not been subjected to the high-temperature sterilizing treatment according to the present invention. Sample Nos. 1 and 2 represent the results obtained on the seeds which have been subjected to the high-temperature sterilizing treatment according to the present invention, which comprises dipping seeds in hot water having a temperature of 70° C. or more for a short period of time, and then dipped in normal temperature water so as to be cooled.

These seeds have been the same kind of seeds subjected to the same specific gravity selection, and they have been reared under the quite same cultivating condition and within the same cultivation room, as represented in Table 1.

TABLE 1

| Sample No. | 1 | 2 | 3 | 4 |
| --- | --- | --- | --- | --- |
| Pretreatment | Specific Gravity Selection | | | |
| Sterilizing Treatment | Dipping Sterilization in Hot Water for Short Time | | not treated | not treated |
| Temperature of Soaking Water | 23° C. | 23° C. | 23° C. | 23° C. |
| Quantity of Occured Putrefaction (per 500 kg of Harvest) | 0.01 kg | 0.3 kg | 12.3 kg | 11.3 kg |

In a case where the seeds were reared after subjected to the high-temperature treatment according to the present invention, as described above, the quantity of putrefied sprouts could be decreased to below several tenth parts as compared with the prior art. Also in the result of the preservation test, the remarkable result could be obtained in the present invention.

The sprouted vegetable seeds sterilizing method according to the present invention comprises exposing seeds to a temperature of 70° C. or more for a short period of time and then quenching the seeds quickly, as described above. By virtue of this method, it is possible to obtain seeds whose putrefaction can be effectively prevented in the rearing of sprouted vegetables. In a case where dry heat such as heated air or combustion gas is used as a high temperature to which seeds are to be exposed, moreover, according to the sprouted vegetable seeds sterilizing method of the present invention, it is possible to preserve seeds as sterilized and to cultivate the seeds as they are, with no fear of deteriorating or putrefying the seeds during the preservation, because their humidity is not increased as in a case where they are treated by wet heat such as hot water.

According to the sprouted vegetables cultivating method of the present invention, furthermore, seeds are used which have been subjected to a sterilizing treatment comprising exposing the seeds to a high temperature of 70° C. or more, as mentioned above. Accordingly, it is possible to rear sprouted vegetables, with their putrefaction remarkably reduced whereby microorganisms breed to a much lesser entent. It is also possible to obtain sprouted vegetables capable of being preserved for a long period of time, because seeds can be cultivated under such a condition that microorganisms breed less, thereby obtaining sprouted vegetables on which microorganisms are less deposited.

In the sprouted vegetables cultivating method according to the present invention, moreover, seeds are cultivated after they have been exposed to a high temperature of 70° C. or more. Accordingly, it is possible to remarkably reduce the breeding of microorganisms because various sterilizing treatments subjected to seeds in the course of their cultivation act effectively upon microorganisms which are weakened by the high-temperature treatment subjected to the seeds.

What is claimed is:

1. A method of sterilizing seeds for sprouts, which comprises exposing said seeds to a temperature in the range of about 70° C. to about 90° C. for a time of about 10 to about 30 seconds, wherein shorter duration is used with higher temperature; and then quenching said seeds to ambient temperature.

2. The method of claim 1, wherein said temperature in the range of about 70° C. to about 90° C. is effected by dry heat.

3. The method of claim 2, wherein said dry heat is effected by heated air or combustion exhaust gases.

4. The method of claim 1, wherein said temperature of about 70° C. to about 90° C. is effected by wet heat.

5. The method of claim 4, wherein said wet heat is effected by hot water.

6. The method of claim 1, wherein said seeds are preheated up to about 45° C. prior to exposing said seeds to a temperature in the range of about 70° C. to about 90° C.

7. The method of claim 1, wherein said quenching is effected by bringing said seeds into contact with air at ambient temperature.

8. The method of claim 1, wherein said quenching is effected by dipping said seeds into water.

9. The method of claim 1, which further comprises, after exposing said seeds to a temperature of about 70° C. to about 90° C., subjecting said seeds to a chlorine treatment.

10. A method of cultivating sprouting seeds, which comprises:

a) subjecting said seeds to a sterilizing treatment comprising exposing said seeds to a temperature in the range of about 70° C. to about 90° C. for a time of about 10 to about 30 seconds, wherein shorter duration is used with higher temperatures;

b) quenching said seeds to ambient temperature; and c) cultivating said sterilized seeds.

11. The method of claim 10, wherein after said quenching step b), a second sterilization step is effected prior to said cultivation step c).

12. The method of claim 10, wherein said temperature of step a) is effected by dry heat.

13. The method of claim 12, wherein said dry heat is effected by heated air or combustion exhaust gases.

14. The method of claim 10, wherein said temperature of about 70° C. to about 90° C. is effected by wet heat.

15. The method of claim 10, wherein said seeds are preheated up to about 45° C. prior to exposing said seeds to a temperature in the range of about 70° C. to about 90° C.

16. The method of claim 10, wherein said quenching is effected by bringing seeds into contact with air at ambient temperature.

17. The method of claim 10, wherein said quenching is effected by dipping said seeds into water.

18. A method of sterilizing sprouting seeds, which comprises exposing said sprouting seeds to a temperature in the range of about 70° C. to about 90° C. for a time of about 10 to about 30 seconds, wherein shorter duration is used with higher temperatures; and then quenching said sprouting seeds with water at a temperature of about 30° to 40° C.

* * * * *